United States Patent
Mathilde van de Loosdrecht et al.

(10) Patent No.: US 12,196,827 B2
(45) Date of Patent: Jan. 14, 2025

(54) METHOD AND APPARATUS FOR DETECTING SUPERPARAMAGNETIC MATERIAL

(71) Applicant: Universiteit Twente, Enschede (NL)

(72) Inventors: Melissa Mathilde van de Loosdrecht, Beemte Broekland (NL); Hendrikus Johannes Gradus Krooshoop, Delden (NL); Bernard ten Haken, Delden (NL); Lejla Alic, Enschede (NL)

(73) Assignee: Universiteit Twente, Enschede (NL)

( * ) Notice: Subject to any disclaimer, the term of this patent is extended or adjusted under 35 U.S.C. 154(b) by 216 days.

(21) Appl. No.: 18/000,514

(22) PCT Filed: Jun. 2, 2021

(86) PCT No.: PCT/EP2021/064779
§ 371 (c)(1),
(2) Date: Dec. 2, 2022

(87) PCT Pub. No.: WO2021/245128
PCT Pub. Date: Dec. 9, 2021

(65) Prior Publication Data
US 2023/0236269 A1    Jul. 27, 2023

(30) Foreign Application Priority Data
Jun. 2, 2020 (NL) .................. 2025726

(51) Int. Cl.
*G01R 33/12* (2006.01)
*A61B 5/06* (2006.01)

(52) U.S. Cl.
CPC .......... *G01R 33/1276* (2013.01); *A61B 5/062* (2013.01)

(58) Field of Classification Search
CPC .. G01R 33/1276; A61B 5/062; G01N 27/745; G01N 27/76
See application file for complete search history.

(56) References Cited

U.S. PATENT DOCUMENTS

| 7,994,786 B2 * | 8/2011 | Weaver ................ A61B 5/05 324/309 |
| 2015/0091556 A1 | 4/2015 | Hong et al. |
| 2018/0100901 A1 | 4/2018 | Choi et al. |

FOREIGN PATENT DOCUMENTS

| WO | WO-03019188 A1 * | 3/2003 | ............. B82Y 25/00 |
| WO | 2018/144599 A1 | 8/2018 | |

OTHER PUBLICATIONS

J. Devkota et al. "Detection of low-concentration superparamagnetic nanoparticles using an integrated radio frequency magnetic biosensor", J. Appl. Phys. 113, 104701 (Mar. 13, 2013) https://doi.org/10.1063/1.4795134 (Year: 2013).*

(Continued)

*Primary Examiner* — Christopher E Mahoney
(74) *Attorney, Agent, or Firm* — N.V. Nederlandsch Octrooibureau

(57) ABSTRACT

The invention relates to a method and apparatus for detecting superparamagnetic material. The method comprises applying, by an excitation coil, a magnetic field during a first period to an object to modulate a magnetization of the superparamagnetic material, the magnetic field comprising a first component with a first frequency; positioning a sensing device at a first position from the excitation coil receiving a first signal by a first detection sub-coil in the sensing device and a second signal by a second detection-sub-coil in the sensing device; determining a sensor signal from the first signal and the second signal; determining a detection signal based on the sensor signal; determining a parameter indicating an amount of superparamagnetic material by dividing (Continued)

the detection signal by the first signal, and repeating steps to at at least one different position in order to determine a location where the parameter has a maximal value.

14 Claims, 4 Drawing Sheets

(56) References Cited

OTHER PUBLICATIONS

A Ferraro et al., "Monitoring Magnetic Nanoparticles in the Body", Materials Science Forum Online: May 19, 2016 ISSN: 1662-9752, vol. 856, pp. 85-91 doi: 10.4028/www.scientific.net/MSF.856.85 (Year: 2016).*

Van De Loosdrecht M.M. et al. "Separation of excitation and detection coils for in vivo detection of superparamagnetic iron oxide nanoparticles", Journal of Magnetism and Magnetic Materials, vol. 475, Dec. 5, 2015, pp. 563-569.

\* cited by examiner

METHOD AND APPARATUS FOR DETECTING SUPERPARAMAGNETIC MATERIAL

FIELD OF THE INVENTION

The invention relates to a method and apparatus for detecting superparamagnetic material.

BACKGROUND

A method for detecting superparamagnetic particles by a separated coil approach is known from "separation of excitation and detection coils for in vivo detection of superparamagnetic iron oxide nanoparticles", by M. M. van de Loosdrecht, S. Waanders, H. J. G. Krooshoop, B. ten Haken Journal of Magnetism and Magnetic Material 475, (2019) 563-569.

That document discloses a device for laparoscopic in vivo detection of superparamagnetic iron oxide nanoparticles, SPIONs. An application for in vivo detection of SPIONs aims at is sentinel node biopsy. This is a method to determine if tumor cells have spread through the body, which helps to improve cancer patient care. The method selectively detects SPIONs using Differential Magnetometry, DiffMag. DiffMag makes use of small magnetic field strengths in the mT range. For DiffMag, a handheld probe is used that contains excitation and detection coils. However, depth sensitivity of a handheld probe is restricted by the diameter of the coils. Therefore, excitation and detection coils are separated in our novel probe. As a result, excitation coils can be made large and placed underneath a patient to generate a sufficiently large volume for the excitation field and the separation of the excitation and the detection coils provide an improved depth sensitivity than that of a handheld probe with the same diameter of detection coils. Detection coils are made small enough to be used in laparoscopic surgery. This method is able to detect small amounts of SPIONs (down to 25 μg Fe), and SPIONs can be measured up to 20 cm from the top of the excitation coil.

A drawback of the known method and device is that the detection of superparamagnetic material is not accurate.

SUMMARY OF THE INVENTION

It is an object of the invention to provide a method and apparatus to improve the detection of superparamagnetic material.

According to a first aspect of the invention this object is achieved by a method for detecting superparamagnetic material comprising:
a) applying a magnetic field during a first period to an object to modulate a magnetization of the superparamagnetic material, the magnetic field comprising a first component with a first frequency;
b) receiving a first signal and a second signal;
c) determining a sensor signal from the first signal and the second signal;
d) determining a detection signal based on the sensor signal; and
e) determining a parameter indicating an amount of superparamagnetic material by dividing the detection signal by the first signal.

In this way the parameter for the amount of superparamagnetic material is compensated for the magnetic field strength at the position of the detection coil in close proximity to the superparamagnetic material and the parameter or count can be used to detect a location of the largest amount of superparamagnetic material with a probe comprising the detection coil.

Furthermore, in this way the typical non-linear characteristic of the magnetization of the superparamagnetic material is measured. This measurement has minimal disturbance of the linear characteristic of paramagnetic material surrounding the probe (for example tissue or plastics) or of influence of the first component.

A further advantage is the typical non-linear behavior of superparamagnetic material occurs at low magnetic field strength that make these methods convenient for use with a human body. For example the magnetic field strength can be in the range from 1 to 10 mT. The first component can be for example, a sine wave with the first frequency of 2525 Hz.

The invention is based on the insight that the amplitudes of the first and second signals generated by the detection coil and thus the detection signal depends on the distance from the superparamagnetic material and the detection coil to the excitation coil. So, for example, signals generated by the detection coil corresponding to a first amount of superparamagnetic material in an object in proximity to the detection coil at a first position at a first distance from the excitation coil can be equal to signals generated by the detection coil corresponding to a second amount, larger than the first amount, of superparamagnetic material in an object in proximity to the detection coil at a second position at a second distance, larger from the first distance.

According to this disclosure the dependency of the detection of the superparamagnetic material on the distance from the superparamagnetic material in close proximity to the probe to the excitation coil is reduced. The method according to this disclosure can be used in a sentinel node method. For example, a user can move a handheld probe comprising the detection coil to detect a location of a sample with the largest amount of superparamagnetic material in a body.

In a particular advantageous embodiment according to this disclosure step c) comprises step c-1) determining a difference signal by subtracting the first signal from the second signal. In this way passive balancing of the first and second signal is obtained an influence of the second component in the sensor signal is reduced.

In a further embodiment according to this disclosure, the method further comprises
c-2) determining intermediate signal from the difference signal with an equal amplitude and a phase difference of 180 degrees with respect to the phase of the difference signal; and
c-3) determining the sensor signal by subtracting the intermediate signal from the difference signal.

In this way active balancing or active compensation is used to obtain the detection signal. An advantage of this step is that an improved SNR can be obtained.

In a further advantageous embodiment according to this disclosure the step of determining of the detection signal comprises
d-1) determining a frequency spectrum of the sensor signal; and
d-2) determining the detection signal based on the frequency spectrum. This class of non-linear methods applies analysis of the frequency spectrum for determining the detection signal and has an advantage of a good signal-to-noise ratio and improved accuracy.

In a further embodiment according to this disclosure the method further comprises
f) applying a second component to the magnetic field during a second period and wherein the second component is a sine wave with a second frequency lower than the first frequency, and the second period is equal to the first period; and wherein the step of determining the detection signal further comprises d-3) determining energies P1, P2 at respectively a sum frequency of the first and two times the second frequency and the difference frequency of the first and two times the second frequency in the frequency spectrum; and d-4) determining the detection signal from an average of the energies P1 and P2.

The second frequency can be for example 30 Hz. In this way an excitation sequence of the first and second components of the magnetic field can be used for frequency mixing of a combination of for example 2525 Hz and 30 Hz sinusoidal fields and the detection signal is obtained from the frequency spectrum. This embodiment provides a sufficient SNR.

In a different embodiment according to this disclosure the method further comprising g) applying a second component to the magnetic field during a second period, wherein the second component is a DC field, and the second period is equal to the first period; and wherein the step of determining the detection signal from the frequency spectrum further comprises d-5) determining energy P3 at the second harmonic of the first frequency of the frequency spectrum; and d-6) determining the detection signal from the determined energy P3.

The field strength of the second component can be, for example, equal to the field strength of the first component. The first frequency F1 can be for example 2525 Hz and the energy P3 is obtained from the frequency spectrum at 5050 Hz. In this way a first method based on Magnetic Particle Spectroscopy, MPS, can be used to determine the detection signal. An advantage of this embodiment is that the DC field is constant, enabling the use of permanent magnets and low power consumption.

In a further different embodiment according to this disclosure the step d) of determining the detection signal further comprises d-7) determining energy P4 at the third harmonic of the first frequency in the frequency spectrum;

d-8) determining the detection signal from the determined energy P4.

The first frequency F1 can be for example 2525 Hz and the energy P4 is obtained from the third harmonic of the first frequency in the frequency spectrum at 7575 Hz. This is a second method based on MPS that can be used to determine the detections signal. An advantage of both the first and this second method based on MPS is because the detection uses the $2^{nd}$ and $3^{rd}$ harmonic frequency a good reduction of the influence of the excitation field on the detection signal can be obtained.

In a further different embodiment according to this disclosure the method further comprises h) applying a second component to the magnetic field during a second period, the second period being smaller than or equal than the first period, and wherein the second component is a square wave with a third period of at least smaller than or equal to the second period and wherein the step d) determining the detection signal comprises d-9) determining a first amplitude of the first component in the difference signal in a first half of the third period;

d-10) determining a second amplitude of the first component in the first difference signal in a second half of the third period d-11) determining the detection signal from the difference in the first and second amplitude.

In this way a differential magnetization detection method can be performed. Phase sensitive detection can be used in steps d4) and d5) to isolates intermediate signals with the first frequency from background noise and the determine the first and second amplitudes.

The first period can be, for example, 1 s, the second period can be 100 ms. and the third period can be, for example, 50 ms.

In a still further embodiment according to this disclosure a direction of the second component of the magnetic field in the second half of a subsequent third period is reversed with respect to the direction of the second component of the magnetic field in the first half of third period. By reversing the direction of the second component in the applied magnetic field in every subsequent third period, magnetic remanence in the material is avoided. A further advantage is that influences due to eddy-currents in other conducting components of the apparatus or conducting elements in the neighboring area and influences of the earth's magnetic field can be reduced.

In a further embodiment according to this disclosure the superparamagnetic material comprises superparamagnetic iron oxide nanoparticles, SPION. A superparamagnetic material comprising SPIONs for introduction in a human body is, for example, Magtrace®, as is available from Endomag, United Kingdom.

According to a second aspect of the invention this object is achieved by an apparatus for detecting superparamagnetic material, comprising:

means arranged to apply a magnetic field comprising a first and a second component to an object;

a sensing device comprising a detection coil; and a controller arranged to:

a) apply a magnetic field during a first period to an object to modulate a magnetization of the superparamagnetic material, the magnetic field comprising a first component with a first frequency;

b) receive, a first signal and a second signal c) determine a sensor signal from the first signal and the second signal;

d) determine a detection signal based on the sensor signal; and e) determine a parameter for an amount of superparamagnetic material by dividing the detection signal by the first signal.

In a further embodiment according to this disclosure the excitation coil comprises a first excitation sub-coil for generating the first component and a second excitation sub-coil for generating the second component.

In a further embodiment according to this disclosure the first excitation sub-coil is coaxially located with respect to the second excitation sub-coil. In this arrangement a flat arrangement of the excitation coil can be obtained.

In a further embodiment according to this disclosure the detection coil comprises a first detection sub-coil and a second detection sub-coil; and the second detection sub-coil is axially arranged with respect to the first detection sub-coil. In this arrangement the balancing of the first detection coil and the second detection coils can be improved.

In a further embodiment according to this disclosure the controller is further arranged to perform the method of any of the claims 2-10.

BRIEF DESCRIPTION OF DRAWINGS

These and other aspects of this disclosure are apparent from and will be elucidated, by way of non-limitative example, with reference to the embodiments described hereinafter and the accompanying drawing.

In the drawing.

DETAILED DESCRIPTION OF EMBODIMENTS

Figure 1:
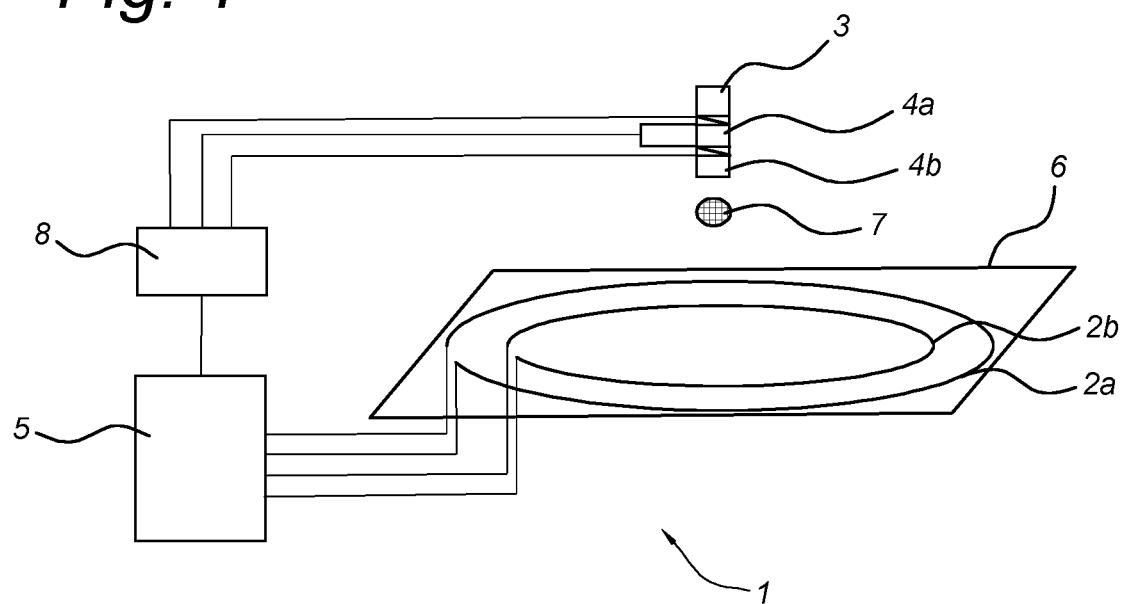
FIG. 1 shows an apparatus according to embodiment according to this disclosure.

The method and apparatus according to this disclosure is explained with respect to FIG. 1 to FIG. 8. In the drawing the same reference signs refer to like objects.

FIG. 1 shows diagrammatically an apparatus according to a first embodiment according to this disclosure for detection of an amount of superparamagnetic material in an object. The superparamagnetic material can be for example, superparamagnetic iron oxide nanoparticles, SPION. A superparamagnetic material for introduction in a human body is, for example, Magtrace®, as is available from Endomag, United Kingdom.

The apparatus 1 comprises the means, for example, an excitation coil for generating a magnetic field. The excitation coil can comprise in a first excitation sub-coils 2a and a second excitation sub-coil 2b. Furthermore, the apparatus comprises a controller 5 connected to the first and second excitation sub-coils 2a, 2b. The controller 5 is further arranged to control the currents through the excitation sub-coils 2a, 2b to generate a magnetic field comprising a first component and a second component. The controller 5 may be further arranged to control the first and second components independently. The apparatus further comprises a support or table 6 provided with the excitation sub-coils 2a, 2b. The dimensions of the support 6 can be such to support a human body.

The apparatus 1 further comprises a sensing device or probe 3 provided with a detection coil. The detection coil can comprise a first detection sub-coil 4a and a second detection sub-coil 4b for receiving signals from the object or sample 7 comprising the amount of superparamagnetic material. The first detection sub-coil 4a and the second detection sub-coil 4b are identical and can be axially arranged in the probe or the sensing device 3. The sensing device can be separated from the table or support and freely moved by a user. The sensing device can also be comprised in a trocar for invasive procedures in a body.

Furthermore, the detection sub-coils 4a, 4b can be connected in series such that a sensor signal can be obtained by subtracting the first signal V1 from the second signal V2 and passive compensation or passive balancing of the first component on the detection coils can be obtained.

In a further embodiment the sensor signal can be obtained by active balancing comprising a balancing circuit arranged to determine an intermediate signal having an equal amplitude and a phase difference of 180 degrees with respect to the phase of the difference signal; and the sensor signal can be obtained by subtracting the intermediate signal from the difference signal.

The apparatus 1 further comprises an analog-to-digital, AD converter 8. The detection sub-coils 4a, 4b are connected with the controller 5 via the analog-digital converter 8. The AD converter 8 converts the sensor signal and the first signal into the digital domain. In an embodiment the apparatus 1 comprises electronic circuits between the detection sub-coils 4a, 4b and the AD converter 8 for signal condition of the sensor signal and the first signal (not shown).

In operation, the controller 5 applies a current through the first excitation sub-coils 2a to generate a magnetic field during a first period to an object to modulate a magnetization of SPIONs, the magnetic field comprising a first component with a first frequency. The first period can be for example 0.5 s. The first frequency can be 2525 Hz and the strength of the first component of the magnetic field for example 4 mT.

The detections coils 2a, 2b receive a first and second signal from the changing flux in the detections coils. A sensor signal is obtained by subtracting the first and second signal. The AD converter 8 converts the sensor signal and the first signal to the digital domain. The controller 5 determines a detection signal based on the sensor signal and a parameter or count indicating an amount of the SPIONs by dividing the detection signal by the first signal. The parameter can be represented by a count having an integer value from 0 . . . N, wherein 0 represents the smallest value and N represents a largest value.

The apparatus 1 and the sensing device 3 can be used for the detection of a position of a small amount of SPIONs in the object 7 using non-linear detection methods. The object can be a sample in body of a patient. For example, this SPION material can be introduced in a body of a patient, after a while the SPION material can be found in sentinel nodes in the body and detected with the apparatus 1 and the probe 3. The detected position of a largest quantity of the SPIONs can then be used in, for example, a Sentinel Lymph Node procedure.

According to this disclosure the dependency on the distance from the location of the amount of SPIONs and the location of the sensing device 3 to the excitation coils is reduced and enables detection of a location of an object comprising a largest amount of SPIONs amongst a plurality of objects comprising different amounts of SPIONs at different positions with respect to the excitation sub-coils 2a, 2b nearly independent from the position of the samples with respect to the excitation sub-coils 2a, 2b. This reduction of dependency is explained in connection with table 1.

TABLE 1

| Distance of object to excitation coils in m | Difference susceptibility | Amplitude first signal | Parameter |
|---|---|---|---|
| 0.1 | 200 | 100 | 2 |
| 0.3 | 10 | 5 | 2 |

In table 1 the distance is defined as the distance of the object or sample, comprising the SPIONs to the first and second excitation sub-coils $2a$, $2b$. The difference in amplitude of the detection signal measured with the sensing device in closer proximity to the object is defined as the difference between the measured susceptibility. The right columns of table 1, including the values of the determined parameter or the count, shows that dependency of the count on the distance of the object to the sub-coils $2a.2b$ is reduced. This method according to this disclosure enables a user to apply the sensing device 3 to detect a sample with the largest amount of SPIONs amongst a number of samples comprising different amounts of SPIONs at different positions from the sub-coils $2a$, $2b$ nearly independent from the position of the samples with respect to the first and second excitations sub-coils $2a$, $2b$.

For example a user can move the sensing device 3 in close proximity to the different samples to detect the sample with the largest amount of SPIONs.

Figure 2:
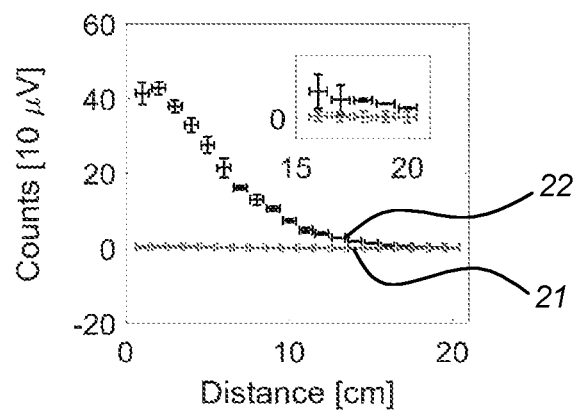
FIG. 2 dependency on the measured magnetization in the object on the distance between the object and the excitation coils.

FIG. 2 shows the dependency of the determined parameter corresponding to an amount of SPIONs in the object at a fixed distance from the object 7 and the sensing device 3 to the excitation sub-coils $2a$, $2b$. The line 21 shows the count of an object that does not comprises SPIONs as a function of the distance from the object and the sensing device to the sub-coils $2a$, $2b$. The curve 22 shows the count of the SPIONS in an object as a function of the distance from the object to the sub-coils $2a$, $2b$.

Figure 3:
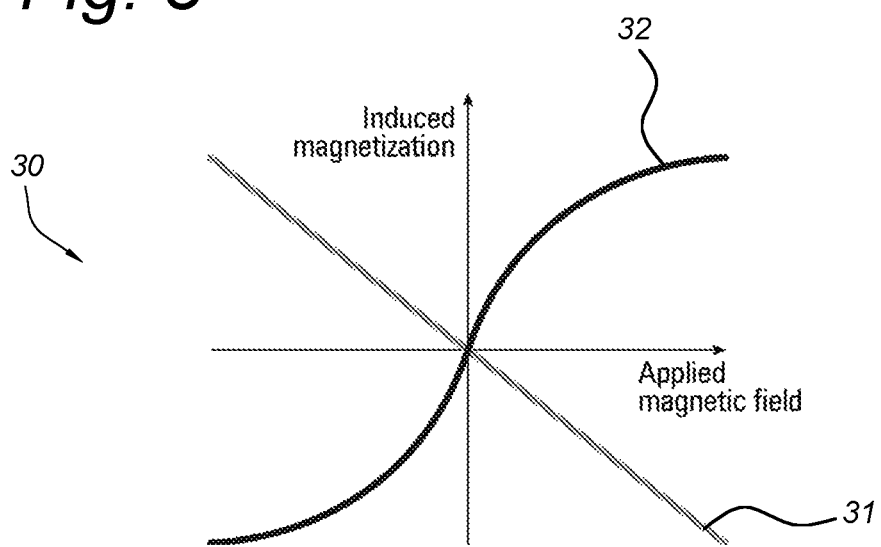
FIG. 3 shows a graph of the magnetization of an object comprising diamagnetic material and SPIONs.

FIG. 3 shows a graph of the magnetization of an object comprising diamagnetic material and SPIONs. The straight line 31 represents a function of the magnetization of diamagnetic material in an object and the applied magnetic field and the S-curve 32 represents a function of the magnetization of the SPIONs and the applied magnetic field in the object. In this disclosure the difference in response between the SPIONs and the diamagnetic material on the applied magnetic field is applied to determine the amount of SPIONs in the sample or cluster of SPIONs in a body or the position of the sample in the body.

In a second embodiment according to this disclosure, the controller 5 further determines a frequency spectrum of the sensor signal, for example by a Digital Fourier Transform or Fast Fourier Transform, and determines the detection signal from the frequency spectrum and the parameter indicating the amount of SPIONs in the body by dividing the detection signal by the first signal.

Alternatively, a lock-in amplifier can be used to determine the detection signal from the sensor signal.

In a third embodiment according to this disclosure the controller performs the steps described herein before with respect to the first and second embodiment to obtain the sensor signal and the frequency spectrum. However, in this embodiment controller applies a further current through the second-excitation sub-coil $2b$ to generate the second component of the magnetic component during a second period, wherein the second component is a sine wave with a second frequency F2 lower than the first frequency F1, and the second period is equal to the first period. So, for example the first frequency F1 can be 2525 Hz and the second frequency F2 can be 30 Hz. The first and the second periods can be 0.5 s. The field strength of the second component is for example 4 times the strength of the first component. So, for example 16 mT.

Thereafter, the controller 5 determines the frequency spectrum from the sensor signal and determines energies P1, P2 at respectively a sum frequency of the first and two times second frequency and the difference frequency of the first and two times the second frequency in the frequency spectrum; and the detection signal from an average of the energies P1 and P2. According to this disclosure, the controller determines the parameter or count of an amount of the SPIONs by dividing the detection signal by the first signal. This mixed frequency method is simple and provides sufficient results for application in the Sentinel Lymph Node Procedure.

Figure 4:
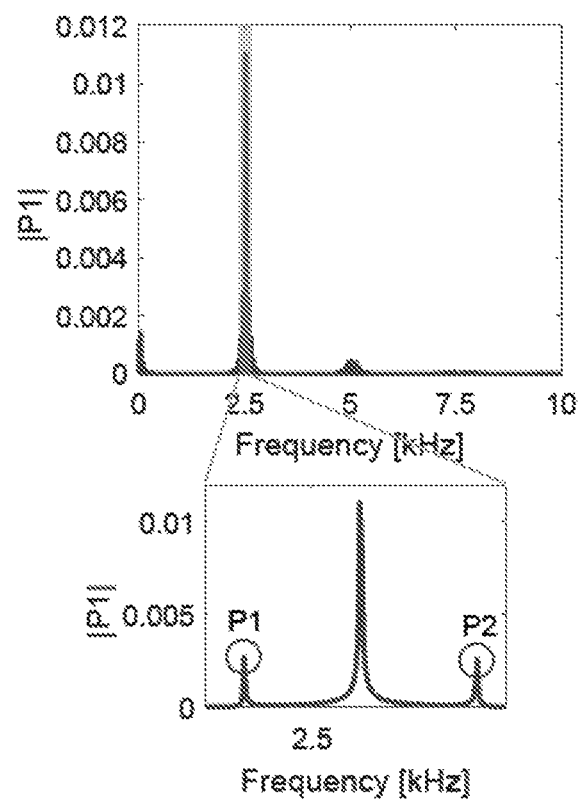
FIG. 4 shows a frequency spectrum of the sensor signal according to the third embodiment for mixed frequency detection.

FIG. 4 shows a frequency spectrum of the sensor signal according to the third embodiment for mixed frequency detection. FIG. 4 shows the energy peaks P1, P2 at the frequencies F1−2F2 and F+2F2 respectively.

In a fourth embodiment according to this disclosure the controller 5 performs the steps of the method as described herein before with respect to the third embodiment to obtain the sensor signal. However, in this embodiment controller 5 applies a DC current through the second ex-citation sub-coil $2b$ to generate the second component of the magnetic component during a second period. Instead of applying the second component of the magnetic field through the second excitation sub-coil, the second component can also applied by a permanent magnet.

The first and the second periods can be 0.5 s. The field strength of the second component is for example 4 times the strength of the first component. So, for example 16 mT. After the detection signal is obtained, the controller 5 determines the frequency spectrum.

Furthermore, in this embodiment the controller 5 determines an energy P3 at the second harmonic of the first frequency of the frequency spectrum and determines the detection signal as the determined energy P3 and the controller determines the parameter or count of an amount of the SPIONs by dividing the detection signal by the first signal. In this way an MPS is achieved with a second harmonic detection. In this embodiment the first frequency is 2525 HZ.

Figure 5:
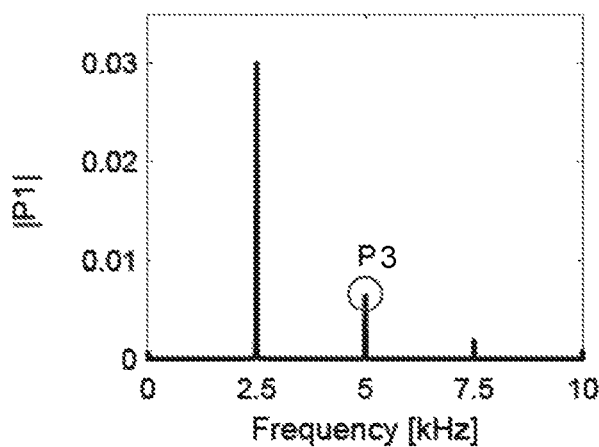
FIG. 5 shows a frequency spectrum of the sensor signal according to the fourth embodiment for second harmonic detection.

FIG. 5 shows a frequency spectrum of the sensor signal according to the fourth embodiment for second harmonic detection. FIG. 5 shows frequency spectrum of the sensor signal with the peak P3 at the second harmonic frequency at 5050 Hz.

A fifth embodiment according to this disclosure the controller 5 performs the steps of the method as described with the first and the second embodiment. In this embodiment no second component of the magnetic field is applied. Furthermore, in this embodiment the controller 5 determines the detection signal as the energy P4 at the third harmonic of the first frequency in the frequency spectrum and the controller determines the parameter or count of an amount of the SPIONs by dividing the detection signal by the first signal. In this way an MPS is achieved including a third harmonic detection. In this embodiment the first frequency can be 2525 Hz.

Figure 6:
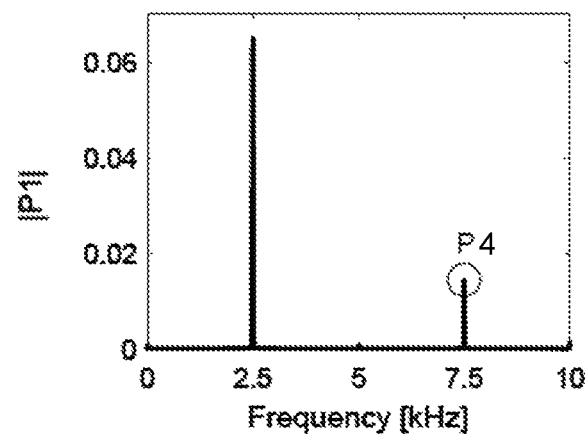
FIG. 6 shows a frequency spectrum of the sensor signal according to the fifth embodiment for third harmonic detection.

FIG. 6 shows a frequency spectrum of the sensor signal according to the fifth embodiment for third harmonic detection. FIG. 6 shows a frequency spectrum of the sensor signal with the peak P4 at the third harmonic frequency at 7575 Hz.

In a sixth embodiment according to this disclosure will be described with respect to the first embodiment. In the fourth embodiment the controller 5 performs the steps of the first embodiment. Furthermore, the controller 5 applies a current though the second excitation sub-coil 2b to generate a second component to the magnetic field during a second period, the second period being smaller than or equal than the first period. So, for example the first period is 0.5 s and the second period is 100 ms. In this embodiment the second component is a square wave with a third period of at least smaller than or equal to the second period. The third period of the square wave can be for example the half of the second period. So, for example 50 ms.

The field strength of the second component is for example 4 times the field strength of the first component and can be for example 16 mT.

Furthermore, the controller determines a first amplitude of the first component in the sensor signal in a first half of the third period and a second amplitude of the first component in the sensor signal in a second half of the third period and determines the detection signal from the difference in the first and second amplitude. In subsequent third periods the controller determines subsequent detection signals and obtains a more accurate detection signal from an average of the determined subsequent detection signals. In a further step the controller determines the parameter or count of an amount of the SPIONs by dividing the detection signal by the first signal.

In a further embodiment the controller 5 applies a current though the second excitation sub-coil 2b to generate the second component during the second half of the subsequent third period, wherein the direction of the second component of the magnetic field during the second half of the subsequent period is reversed with respect to the direction of the second component of the magnetic field applied in the first half of the third period. In this way a so-called Differential Magnetometry method is obtained.

By reversing the direction of the second component in the applied magnetic field every second period, magnetic remanence in the material is avoided. A further advantage is that influences due to eddy-currents in other conducting components of the apparatus or conducting elements in the neighboring area and influences of the earth's magnetic field can be reduced.

Figure 7A:
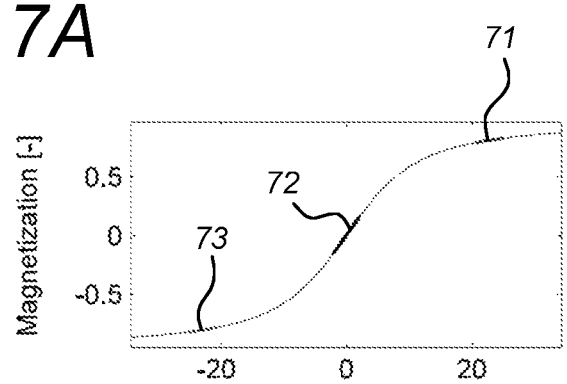
FIG. 7A shows the S-curve representing the magnetization of SPIONS as function of the excitation magnetic field.

FIG. 7A shows the S-curve representing a function of the magnetization of SPIONS and the excitation magnetic field according to this embodiment.

FIG. 7A shows the sections 71, 72, 73 of the magnetization curve that are selected to generate the detection signals in the detection coils 2a, 2b according to sixth embodiment according to this disclosure.

Figure 7B:
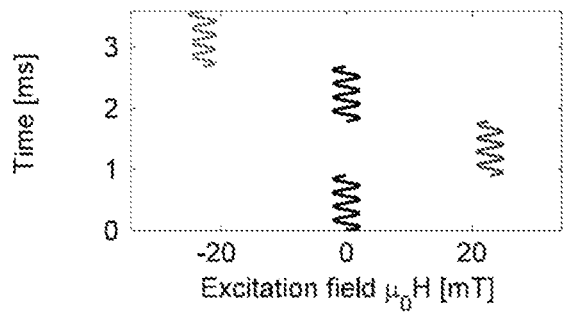
FIG. 7B shows the excitation field of a magnetization curve and sections of the magnetization curve.

FIG. 7B shows the excitation magnetic field along a corresponding horizontal axis as FIG. 7A as a function of time along the Y-axis.

FIG. 7B shows the corresponding offsets obtained by the second component in the excitation field to excite these sections 71, 73 of the magnetization curve of FIG. 7A.

Figure 8A:
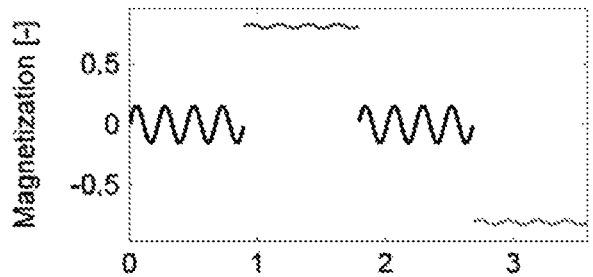
FIG. 8A shows the magnetization as a function of time during subsequent second periods of the second component of the excitation magnetic field.

FIG. 8A shows the magnetization as a function of time during subsequent periods of the second component of the applied magnetic field. FIG. 8A shows that the modulation of the magnetization due to the magnetic field is smaller in the periods 1-2 ms and 3-4 ms, wherein the second component is applied, compared to the modulation in the magnetization due to the first component in the period 0-1 ms and 2-3 ms wherein the second components is nil.

Figure 8B:
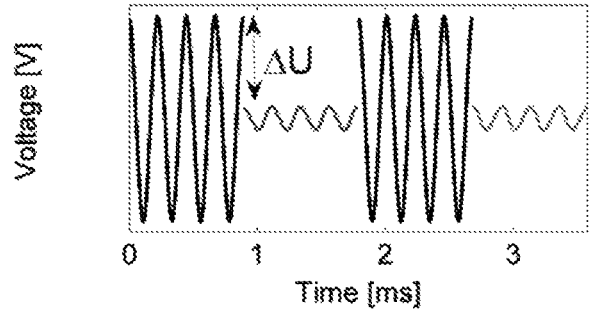
FIG. 8B shows the different modulations of the generated signals in the detection coils.

FIG. 8B shows the difference AU between the modulations of the signals generated in the detection coils 4a, 4b in a period wherein the second component has a magnetic field strength to cause a small deviation of the magnetization from an initial state.

Both FIG. 8a and FIG. 8B show the modulation of the magnetization of the SPIONs and signals generated in the detection coils 4a, 4b respectively in an embodiment, wherein in a subsequent third period the direction of the second component is reversed with respect to direction of the applied second magnetic field in the preceding third period.

Each of the foregoing elements of the apparatus according to the present disclosure may be configured with one or more components, names of which may vary with a type of the apparatus. The apparatus may include at least one of the foregoing elements, some of which may be omitted or to which other elements may be added. In addition, some of the elements of the apparatus according to various embodiments may be integrated into one entity to perform functions of the corresponding elements in the same manner as before they are integrated.

Although the invention is described using specific embodiments, it will be clear that multiple methods and arrangements are possible within the scope of the invention. The skilled person will be able to combine, adapt, change or leave out one or more of the disclosed specific features of the embodiments.

The invention claimed is:

1. A method for detecting superparamagnetic material comprising:
    a) applying, by an excitation coil, a magnetic field during a first period to an object to modulate a magnetization of the superparamagnetic material, the magnetic field comprising a first component with a first frequency;
    a-2) positioning a sensing device (3) at a first position from the excitation coil
    b) receiving a first signal by a first detection sub-coil (4a) in the sensing device (3) and a second signal by a second detection-sub-coil (4b) in the sensing device (3);
    c) determining a sensor signal from the first signal and the second signal;
    d) determining a detection signal based on the sensor signal;
    e) determining a parameter indicating an amount of superparamagnetic material by dividing the detection signal by the first signal, and
    f) repeating steps (a-2) to (e) at at least one different position in order to determine a location where the parameter has a maximal value.

2. The method according to claim 1, wherein step c further comprises step c-1) determining a difference signal by subtracting the first signal from the second signal.

3. The method according to claim 2, further comprising wherein step c) further comprises
    c-2) determining an intermediate signal having an equal amplitude and a phase difference of 180 degrees with respect to the phase of the difference signal; and
    c-3) determining the sensor signal by subtracting the intermediate signal from the difference signal.

4. The method according to claim 1, wherein step d) the determining of the detection signal comprises
    d-1) determining a frequency spectrum of the sensor signal;
    d-2) determining the detection signal based on the frequency spectrum.

5. The method according to claim 4 further comprising
f) applying a second component to the magnetic field during a second period, wherein the second component is a sine wave with a second frequency lower than the first frequency, and the second period is equal to the first period; and wherein the step of determining the detection signal further comprises
   d-3) determining energies P1, P2 at respectively a sum frequency of the first and two times second frequency and the difference frequency of the first and two times second frequency in the frequency spectrum; and
   d-4) determining the detection signal from an average of the energies P1 and P2.

6. The method according to claim 4, wherein the method further comprising
g) applying a second component to the magnetic field during a second period,
wherein the second component is a DC field, wherein the second period is equal to the first period;
and wherein the step of determining the detection signal comprises
   d-5) determining energy P3 at the second harmonic of the first frequency in the frequency spectrum; and
   d-6) determining the detection signal from the determined energy P3.

7. The method according to claim 4, wherein the step d) determining the detection signal further comprises
   d-7) determining energy P4 at the third harmonic of the first frequency in the frequency spectrum; and
   d-8) determining the detection signal from the determined energy P4.

8. The method according to claim 1, wherein the method further comprising
h) applying a second component to the magnetic field during a second period, the second period being smaller than or equal than the first period, wherein the second component is a square wave with a third period of at least smaller than or equal to the second period; wherein the step d) determining the detection signal comprises
   d-9) determining a first amplitude of the first component in the sensor signal in a first half of the third period;
   d-10) determining a second amplitude of the first component in the sensor signal in a second half of the third period; and
   d-11) determining the detection signal from the difference in the first and second amplitude.

9. The method of claim 8, wherein a direction of the second component of the magnetic field in the second half of a subsequent third period is reversed with respect to the direction of the second component of the magnetic field in the first half of third period.

10. The method of claim 1, wherein the superparamagnetic material comprises superparamagnetic iron oxide nanoparticles, SPION.

11. An apparatus for detecting superparamagnetic material, comprising:
   an excitation coil arranged to apply a magnetic field comprising a first and a second component to an object;
   a sensing device (3) comprising a first detection sub-coil (4a) and a second detection sub-coil (4b); and
   a controller arranged to:
   a) apply, by the excitation coil, a magnetic field during a first period to an object to modulate a magnetization of the superparamagnetic material, the magnetic field comprising a first component with a first frequency;
   a-2) position the sensing (3) at a first position from the excitation coil,
   b) receive, a first signal by the first detection sub-coil (4a) in the sensing device (3) and a second signal by the second detection sub-coil (4b) in the sensing device (3);
   c) determine a sensor signal from the first signal and the second signal;
   d) determine a detection signal based on the sensor signal; and
   e) determine a parameter indicating an amount of superparamagnetic material by dividing the detection signal by the first signal, and
   f) repeat steps (a-2) to (e) at at least one different position in order to determine a location where the parameter has a maximal value.

12. The apparatus of claim 11, wherein the excitation coil comprises a first excitation sub-coil for generating the first component and a second excitation sub-coil for generating the second component.

13. The apparatus of claim 12, wherein the first excitation sub-coil is coaxially arranged with respect to the second excitation sub-coil.

14. The apparatus according to claim 11, wherein the detection coil comprises a first detection sub-coil and a second detection sub-coil, and the second detection sub-coil is axially arranged with respect to the first detection subcoil.

* * * * *